(12) United States Patent
Nanavati et al.

(10) Patent No.: US 9,510,878 B2
(45) Date of Patent: Dec. 6, 2016

(54) PRE-CURVED INTRAMEDULLARY CLAVICLE NAIL AND METHOD OF USING SAME

(75) Inventors: Vipul N. Nanavati, Towson, MD (US); James M. Paci, East Setauket, NY (US); Frederick W. Werner, Fayetteville, NY (US); Levi G. Sutton, Chicago, IL (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 111 days.

(21) Appl. No.: 13/510,241

(22) PCT Filed: Nov. 16, 2010

(86) PCT No.: PCT/US2010/056814
§ 371 (c)(1),
(2), (4) Date: Oct. 11, 2012

(87) PCT Pub. No.: WO2011/060412
PCT Pub. Date: May 19, 2011

(65) Prior Publication Data
US 2013/0035689 A1 Feb. 7, 2013

Related U.S. Application Data

(60) Provisional application No. 61/261,396, filed on Nov. 16, 2009.

(51) Int. Cl.
*A61B 17/72* (2006.01)
(52) U.S. Cl.
CPC ....... *A61B 17/7291* (2013.01); *A61B 17/7208* (2013.01)

(58) Field of Classification Search
CPC . A61B 17/72; A61B 17/7208; A61B 17/7216; A61B 17/7225; A61B 17/7233; A61B 17/725; A61B 17/7283
USPC ...................................... 606/62–64
See application file for complete search history.

(56) References Cited

U.S. PATENT DOCUMENTS

| 2,579,968 A | 12/1951 | Rush |
| 3,760,802 A | 9/1973 | Fischer et al. |
| 3,779,239 A | 12/1973 | Fischer et al. |

(Continued)

FOREIGN PATENT DOCUMENTS

| DE | 19912696 A1 | 10/2000 |
| EP | 1808143 A1 | 7/2007 |

(Continued)

OTHER PUBLICATIONS

International Search Report & Written Opinion for PCT/US2010/056814.

(Continued)

*Primary Examiner* — Eduardo C Robert
*Assistant Examiner* — Julianna N Harvey
(74) *Attorney, Agent, or Firm* — Hoffmann & Baron, LLP (57) ABSTRACT

The present invention relates to an intramedullary nail surgically inserted into a long bone, especially the clavicle. Specifically, the present invention is directed to a curved rod that accommodates the majority of human anatomies and is insertable and capable of either being permanently retained therein or removed if desired.

21 Claims, 5 Drawing Sheets

(56) References Cited

U.S. PATENT DOCUMENTS

| | | | |
|---|---|---|---|
| 4,055,172 A * | 10/1977 | Ender | A61B 17/921 606/62 |
| 4,854,312 A | 8/1989 | Raftopoulos et al. | |
| 4,877,019 A | 10/1989 | Vives | |
| 5,034,012 A | 7/1991 | Frigg | |
| 5,053,035 A | 10/1991 | McLaren | |
| 5,879,352 A | 3/1999 | Filoso et al. | |
| 5,976,137 A | 11/1999 | Mayer | |
| 6,338,732 B1 | 1/2002 | Yang | |
| 7,425,213 B2 | 9/2008 | Orbay | |
| 2005/0027294 A1 * | 2/2005 | Woll | A61B 17/7291 606/62 |
| 2005/0065520 A1 | 3/2005 | Orbay | |
| 2005/0216007 A1 | 9/2005 | Woll et al. | |
| 2006/0122601 A1 | 6/2006 | Tandon | |
| 2008/0306479 A1 | 12/2008 | Bernstein | |
| 2009/0069812 A1 | 3/2009 | Gillard et al. | |
| 2009/0287213 A1 * | 11/2009 | Pieske | 606/62 |
| 2010/0023010 A1 * | 1/2010 | Nelson | A61B 17/1717 606/62 |
| 2010/0114097 A1 * | 5/2010 | Siravo | A61B 17/686 606/62 |

FOREIGN PATENT DOCUMENTS

| | | |
|---|---|---|
| RU | 2 055 538 C1 | 10/1996 |
| RU | 2 266 072 C1 | 12/2005 |
| SU | 1175460 A | 10/1983 |
| SU | 1175460 A1 | 8/1985 |
| WO | 2009/094478 A1 | 7/2009 |

OTHER PUBLICATIONS

Kettler, Mark et al., "Flexible Intramedullary Nailing for Stabilization of Displaced Midshaft Clavicle Fractures : Technique and results in 87 patients," Acta Orthopaedica, 78:3, pp. 424-429 http://www.informaworld.com/smpp/title~content=t713400243.

Dahners, L E., "Antegrade Clavicle Nailing," J Orthop Trauma, 19:7 (2005), pp. 501-502 http://journals.iww.com/jorthotrauma/Citation/2005/08000/OPINION__Antegrade_Clavicle_Nailing.15.aspx.

Extended European Search Report, EP 10 83 0898.2 mailed May 22, 2014.

* cited by examiner

PRE-CURVED INTRAMEDULLARY CLAVICLE NAIL AND METHOD OF USING SAME

CROSS-REFERENCE TO RELATED APPLICATIONS

The present invention is the national stage filing of International Application No. PCT/US2010/056814, filed Nov. 16, 2010, which claims priority to U.S. Provisional Application No. 61/261,396, filed Nov. 16, 2009, the entire contents of each of which are incorporated by reference herein.

FIELD OF THE INVENTION

The present invention relates to an intramedullary nail surgically inserted into a long bone, especially the clavicle. Specifically, the present invention is directed to a curved rod that accommodates the majority of human anatomies and is insertable and capable of either being permanently retained therein or removed if desired.

RELATED ART

Clavicle fractures have generally been treated either non-operatively or with plate fixation. However, these methods suffer from serious defects. For example, non-operative treatment generally takes a far longer time to heal, and may not result in a fully healed bone. In addition, non-operative treatment has been found to lead to some form of malunion (non-anatomic alignment) deformity, which may ultimately lead to shoulder dysfunction. Surgical treatment is preferred, and provides additional advantages, for example, there is decreased pain, early return to functionality of the extremities, decreased risk of deformity, and high rates of union. However, disadvantages of plate fixation, for example, include prominence of large hardware, and the subsequent need for removal of the hardware due to discomfort experienced by the patient. In addition, insertion of such hardware requires a fairly large incision, which results in an undesirable scar cosmesis and further runs the risk of severing nerves in the surgical site and chest wall. Further, there exist potential risks of de-vascularization of the fracture environment during the surgical explores leading to the risk of nonunion.

The concept of an intramedullary nail has been met with poor success. One main reason for the lack of success is that these prior nailing systems have lacked the appropriate anatomic consideration for curvature and length of the clavicle in the patient. These prior nails have been generally straight and rigid nails that did not take into consideration the natural curvature of the clavicle as it courses from medial to lateral resulting in discomfort as well as improper healing. In addition, prior art nails have not been secured properly, and have frequently faced complications of implant migration, misalignment due to implant constraints, and rotational instability about the fracture site.

The present invention provides a clavicle nail system which is capable of being implanted in a minimally invasive manner and which solves the problems of the prior art.

SUMMARY OF THE INVENTION

The pre-curved intramedullary nail of the present invention addresses the previous problems, including migration, restoring anatomic alignment by considering the appropriate curvature and anatomy of the clavicle, and preventing rotational instability by creating a fixed angle locking construct and the ends of the clavicle via screw fixation. In addition, the pre-curved intramedullary nail of the present invention would avoid large incisions thereby addressing important patient considerations such as scar cosmesis. The present invention avoids hardware prominence as it is intramedullary and thereby avoids the almost expected need for a second surgical procedure to remove the implant, as is common with plate fixation. Finally, by avoiding excessive dissection and about the fracture site, the present invention also decreases the risk of nonunion, as the biologic environment about the fracture would be minimally disturbed.

In one embodiment of the present invention, there is provided an intramedullary device, including a pre-curved rod having a proximal end and a distal end, defining a nail body therebetween, the nail body having a longitudinal axis and a radial axis; and a fixation site at each of the proximal and distal ends.

In another embodiment, there is provided a method of implanting a pre-curved, intramedullary nail into a canal of a clavicle; including the steps of: providing a intramedullary nail having a first end and a second end, the ends defining a curved rod therebetween, the intramedullary nail having a fixation site towards each of the first and second ends of the nail; implanting the intramedullary nail into a cavity of a curved bone having a fracture site separating the curved bone into a first segment and a second segment, such that the intramedullary nail extends across the fracture site; fixing the intramedullary nail at the first segment and the second segment with at least one fixation device at each fixation site of the intramedullary rod.

In other aspects of the invention, there is provided a system for intramedullary nail implantation, including: an intramedullary nail; at least one fixation device; and a means for observing positioning of the nail during implantation.

The above-referenced advantages, as well as other advantages, of the present invention will become more apparent from the following detailed description in combination with the following drawings.

DETAILED DESCRIPTION OF THE INVENTION

The human clavicle bone extends substantially along the shoulder, from the sternum to the end of the shoulder. As with any bones of the human body, the clavicle is susceptible to breaking and thus in need of repair. Typically, clavicle breaks occur in the mid-region of the clavicle, separating the clavicle into two separate portions. Repair of the clavicle requires a method and apparatus to hold the two separate portions together so the bone may heal in an anatomical orientation. The present invention is an intramedullary nail that allows for insertion of the nail through the medullary cavity of the clavicle (also referred to as the medullary canal). As used herein, the terms "subject", "patient" and "human" may be used interchangeably to refer to the individual into whom the inventive nail is to be implanted. The terms "implanter", "user" and "doctor" may be used interchangeably to refer to the individual who actually implants the device into the subject. Obviously, there may be more than one individual who implants the device, but for ease of reference, the singular form of these words will be used herein.

Figure 1:
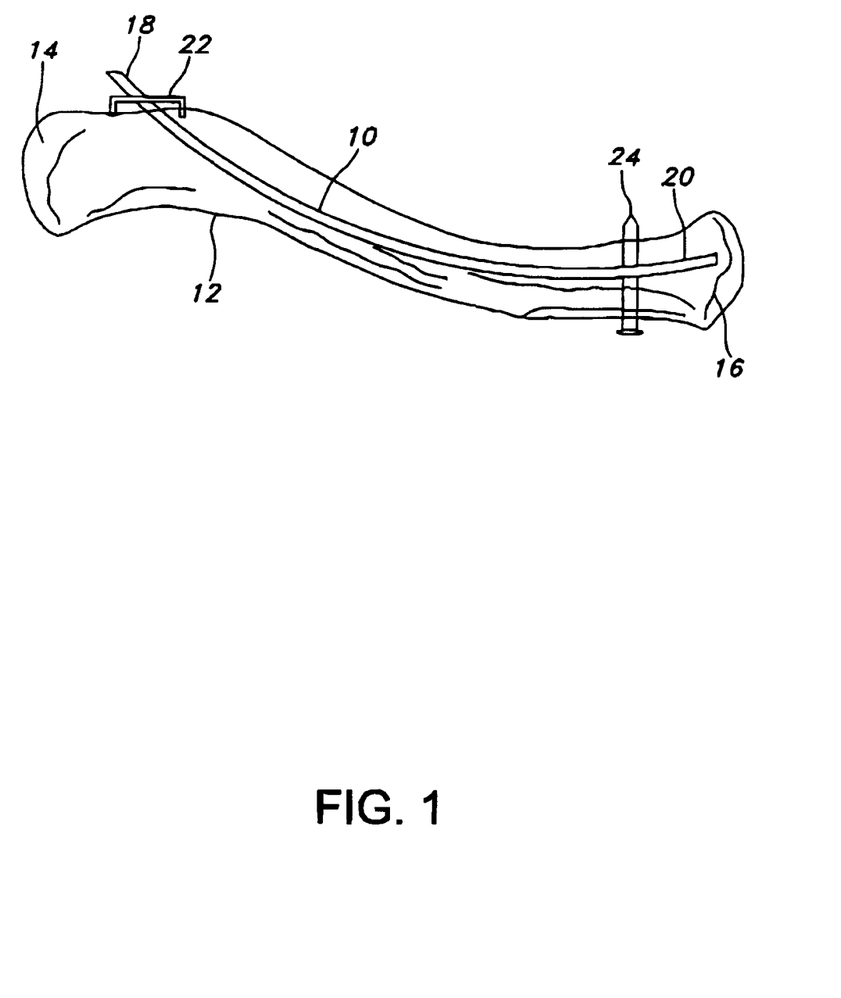
FIG. 1 is a cross sectional view of the clavicle with the intramedullary nail of the present invention implanted therein.
Figure 2A:
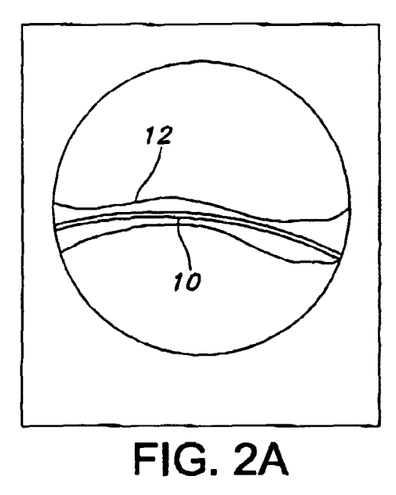
FIGS. 2A-2B are radiographs of an intact clavicle with the intramedullary nail of the present invention inserted therein.
Figure 2B:
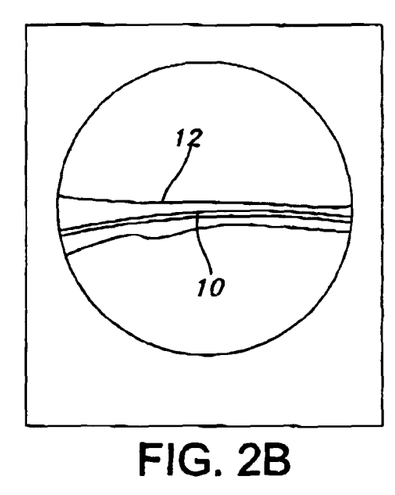
Figure 2C:
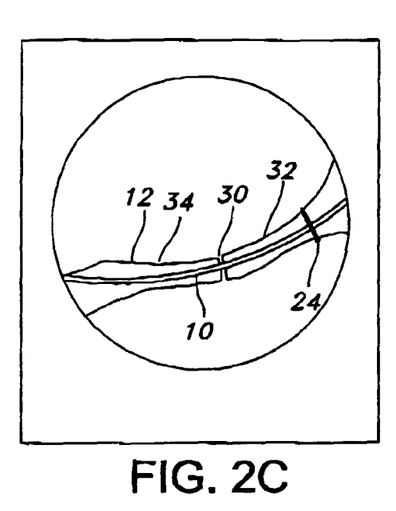
FIGS. 2C-2D are radiographs of clavicle having a midshaft fracture with the intramedullary nail of the present invention inserted therein.
Figure 2D:
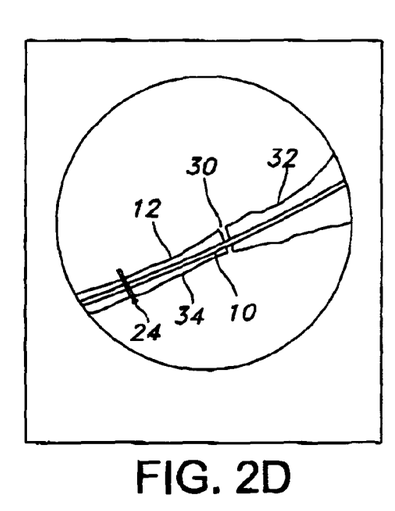

As can be seen in FIG. 1, the nail 10 is capable of being inserted through the medullary cavity of the clavicle 12. The medullary cavity of the clavicle 12 may be referred to herein as the "nail path", since this is the path along which the nail 10 travels during insertion. An important feature of the inventive nail 10 is that it has a curved structure, allowing the nail 10 to extend through the clavicle 12 from the shoulder end 14 to the sternum end 16. The nail 10 may be pre-curved or a user may curve the nail 10 to the desired radius, as will be described in more detail below. Desirably, the curve extends the length of the nail 10, extending from the proximal end 18 to the distal end 20. As used herein, the term "distal end" shall refer to the end of the nail 10 that is inserted into the bone and therefore is furthest from the doctor during implantation. The term "proximal end" shall refer to the end of the nail 10 that is closest to the doctor during implantation.

Figure 3A:
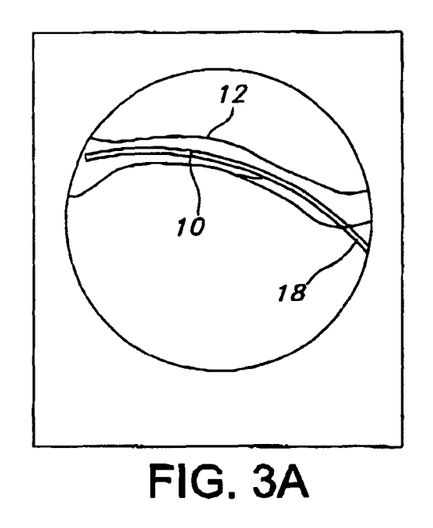
FIGS. 3A-3B are radiographs of the clavicle with the intramedullary nail of the present invention inserted therein.
Figure 3B:
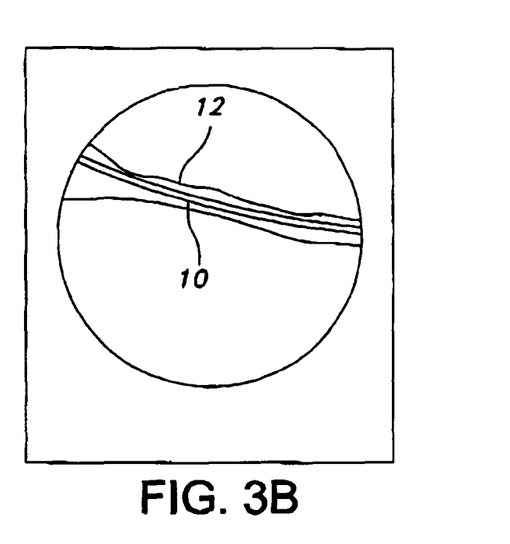
Figure 3C:
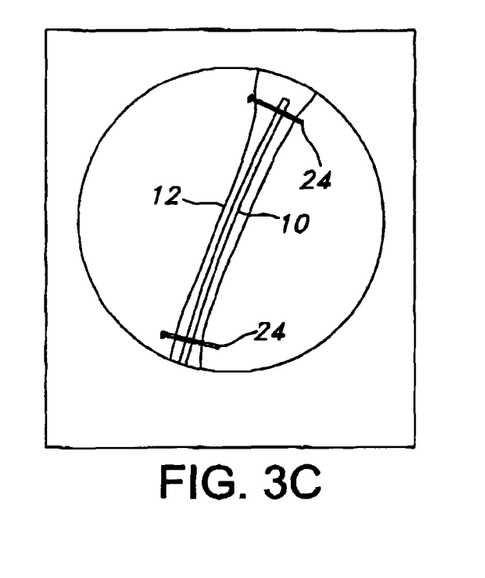
FIG. 3C is a radiograph of a clavicle with the intramedullary nail of the present invention inserted therein and fixated by two substantially parallel screws.

The inventive intramedullary nail 10 may be easily inserted into a clavicle 12 and anchored in place by any desired fixation method. FIG. 1 demonstrates two typical fixation methods: a bone screw 24 and a bone staple 22. Preferably, the nail 10 is held in place by at least two bone screws 24, which will be discussed in further detail below. FIGS. 2-3 depict various radiographs of clavicles having the nail 10 of the present invention implanted therein. Specifically with respect to FIGS. 2C-2D, the clavicle 12 is depicted with a fracture 30 separating the clavicle 12 into two segments, the lateral segment 34 (closest to the patient's shoulder) and the medial segment 32 (closest to the patient's sternum). In these Figures, the nail 10 can be seen to connect the two segments 32 and 34 of the clavicle 12 together to promote healing.

The intramedullary nail 10 of the present invention may be implanted into any bone of the patient, but preferably is designed to be implanted into the clavicle 12. The nail 10 may be constructed of any desired material, and most preferably is made of a material that is safe for use inside a human patient. Such materials include those that are approved by the FDA or any other regulatory agency for implantation into humans. The materials should be lightweight but capable of withstanding pressure, rotation, weight and other forces thereon. Desired materials include titanium, stainless steel, and combinations thereof. In some embodiments, the nail may include components made of plastic or other inert material. Desirably, the nail 10 is made of a material that is pliable and will allow some flexure, but not so flexible that insertion is made difficult or complicated. A degree of flexibility is helpful during insertion to allow for the nail 10 to adjust to various curves within the cavity of the clavicle 12.

The intramedullary nail 10 is desirably sized so as to conform to the natural curve of the cavity of the clavicle 12. As will be understood by those of skill in the art, the shape and size of the clavicle 12 in different individuals will vary from patient to patient. The present invention is designed to account for these differences, and may be modified as necessary.

The applicants have discovered that in the majority of humans, the clavicle 12 cavity has a curve that has a radius of approximately 60 to 180 mm, and more particularly between 80-150 mm. In an even higher majority of humans, the clavicle 12 has a cavity that has a radius of curvature of about 80 to about 120 mm. Thus, the present invention includes a nail 10, having a radius of curvature of from about 60 to about 180 mm, more specifically from about 80 to about 150 mm, more specifically from about 80 to about 120 mm, and even more specifically about 120 mm. The radius of curvature may be altered slightly to conform more specifically to the individual patient. For example, slight adjustment to the curvature of the nail 10 may be performed in the operating room, prior to insertion into the patient.

In addition, the applicants have discovered that, in the majority of humans, the clavicle 12 cavity has a length of about 85-155 mm, and more specifically about 95 to about 135 mm. Most specifically, the cavity of the clavicle 12 is about 100-130 mm in length. Thus, the inventive nail 10 may have a length suitable for the particular cavity in the patient, and may be about 70 mm to about 155 mm in length, may be about 95 mm to about 130 mm in length, or may be about 100 mm to about 130 mm in length. In a preferred embodiment, the nail 10 has a length that is between about ⅔ and about ¾ the length of the cavity of the clavicle 12. It may be desirable, of course, to insert the nail 10 only partially through the cavity of the clavicle 12, in which case the length of the nail 10 may be modified by the user. For example, slight adjustment to the length of the nail 10 may be performed in the operating room, prior to insertion into the patient. In some embodiments, it may be desirable to have a nail 10 that is longer than the average patient (i.e., longer than about 100 mm to about 130 mm), so that it may be cut or otherwise manipulated prior to insertion into the patient.

As is clearly understood by those of skill in the art, the lengths and degrees of radius provided herein are suitable for the majority of adult humans. However, lengths, wall thicknesses, canal diameters, curvatures and other characteristics of various individuals may vary, and thus the nail 10 of the present invention may be modified to take such considerations into account. Further, the nail 10 of the present invention may be modified to account for the size of a child's clavicle bone, and would therefore have a smaller length, for example. Thus, the present invention may include an intramedullary nail 10 which is precurved to conform to a majority of a pediatric clavicle curvature. Other characteristics, such as the degree of curvature and cross-sectional size and shape may be varied as necessary.

Figure 4A:
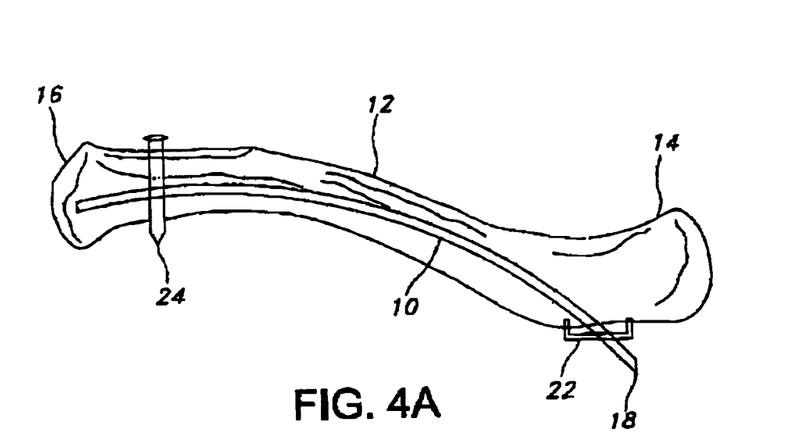
FIG. 4A is a drawing of a clavicle with the intramedullary nail of the present invention inserted therein and demonstrating two fixation methods.
Figure 4B:
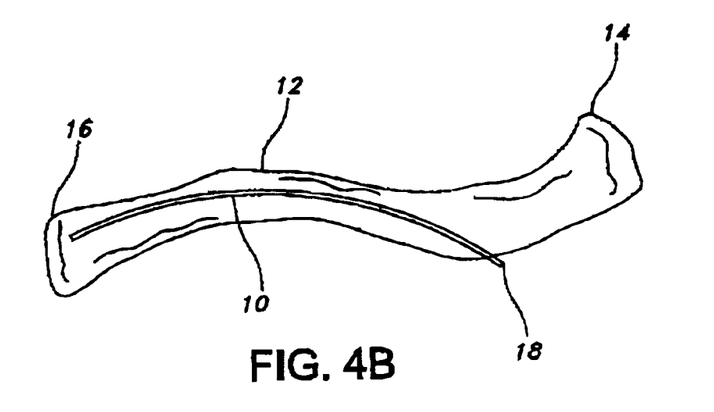
FIG. 4B is a drawing of a second clavicle with the intramedullary nail of the present invention inserted therein.

In one particular embodiment, the nail 10 has a length that allows for the proximal end 18 to remain outside the cavity of the clavicle 12. As may be seen, for example, in FIG. 1, the proximal end 18 of the nail 10 is outside the cavity of the clavicle 12. This may allow for the user to grasp the nail 10 after insertion, either to remove the nail 10 completely, to adjust placement of the nail 10, or to manipulate the nail 10 in any other fashion. For example, after insertion, it may be desirable to remove the nail 10 for any number of reasons. Allowing the proximal end 18 to stick out the cavity may be useful to remove the nail 10 without invasive surgery or other potentially harmful and painful techniques. As can be seen in the drawings of FIGS. 4A and 4B, the proximal end 18 of the nail 10 may stick out from the clavicle 12 any desired length. FIG. 4A depicts the proximal end 18 sticking out a length that is further than that shown in FIG. 4B. The length by which the proximal end 18 remains outside the clavicle 12 is entirely up to the discretion of the individual implanting the nail 10.

The nail 10 may be any shape desired, including variations in the shape of the curvature and the cross-sectional shape of the nail 10. In some embodiments, the nail 10 has a cylindrical cross-sectional shape. It may have an elliptical cross section, or it may have a cross section that is substantially elliptical, but includes flattened ends to aid in securement of the nail 10. The cross section can vary in size along the nail's length as desired, for example tapering or flaring as may be necessary. The distal end 20 of the nail 10 is preferably blunted, but may be flat. The distal end 20 may include a conical end; however, it is most desirable that the distal end 20 not be sharp or pointed. Since the distal end 20 is the end that is inserted into the cavity of the clavicle 12, use of a pointed or sharp end may pierce the interior of the clavicle 12, causing pain, discomfort, and severely damaging the patient. The proximal end 18 may be any shape desired, and in some embodiments may be flared, so as to prevent inadvertent insertion into the patient or to provide an alternative means of fixation. In some embodiments, the proximal end 18 may include a handle or other grip which may aid the user in inserting the nail 10 into the patient. The handle or grip may be affixed to the nail 10, or it may be removable. It may be desirable to include an end cap which may be attached and/or attachable on the proximal end 18 of the device after implantation.

Desirably, the cross-section of the nail 10 is slightly smaller than the diameter of the cavity of the clavicle 12. For example, it may be preferable that the nail 10 have a diameter that is about 1 to about 4 mm smaller than the diameter of the cavity of the clavicle 12. In this fashion, the nail 10 will not completely and fully fill the cavity of the bone. The use of a nail 10 having a slightly smaller cross section is useful during implantation of the nail 10, as the nail 10 will be allowed to travel through the cavity and into place. It is preferred that the nail 10, once implanted, will lie against at least two and most desirably three points of the inner cortical abscess of the bone into which it is implanted. Since the nail 10 has a smaller cross section than the cavity, however, it is desirable to affix the nail 10 into place once it is implanted. The intramedullary nail 10 may be hollow, solid, or have regions that are hollow and regions that are solid.

The nail 10 may be fixed in place after it has been implanted into the clavicle 12 by any desired means. In some embodiments, it may be preferable to affix the nail 10 in place via bone screws, staples, nails, or any known fixation means. As can be seen in FIGS. 1 and 3C, for example, the fixation may include a bone screw 24 and/or a bone staple 22. The nail 10 desirably includes at least one fixation site at a location near the proximal end 18 and a second fixation site at a location near the distal end 20. The fixation site(s) may include one or more holes drilled through the nail 10. The nail 10 may include holes that are pre-drilled to allow the fixation device to hold it in place, or the nail may drilled immediately before, during or after implantation of the nail 10. The fixation device(s) [i.e., staples, screws, nails, etc.] may be inserted through the bone and into the nail 10. It may be desired to have the fixation device(s) extend completely through the nail 10 and into the bone for full affixation.

In one embodiment, best seen in FIG. 3C, the nail 10 may be held in place by a plurality of bone screws 24. The nail 10 should be held in place by at least two screws 24, but may be held in place by more than two screws 24. As seen in FIG. 3C, two bone screws 24 are inserted through the clavicle and are fed through the nail at two locations of the nail 10. Most desirably, the screws 24 (or other fixation devices) hold the nail 10 in place at a location near the proximal end 18 and at a location near the distal end 20, within the cavity of the clavicle 12.

Figure 5:
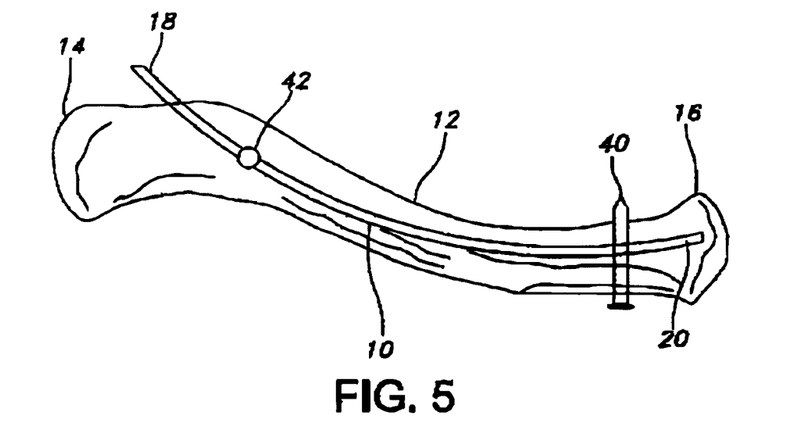
FIG. 5 is a cross-section view of the clavicle with the intramedullary nail of the present invention inserted therein and fixated by perpendicular screws.

In a particularly preferred embodiment, depicted in FIG. 5, the nail 10 of the present invention desirably is held in place by two bone screws in substantially perpendicular directions, with one screw located near the proximal end 18 of the nail 10 and the other located near the distal end 20 of the nail 10. Use of fixation devices that are in different directions (i.e., substantially perpendicular) may be useful in reducing rotational torsion that may affect the nail 10. As may be appreciated by one of skill in the art, the clavicle is subjected to a series of rotational and torsional stresses, for example when a person moves or rotates his or her arm, stresses are exerted on the clavicle. The affixation with fixation devices in different directions, such as substantially perpendicular, aids in preventing the rotation and limiting the distribution of changes and forces that go across the fixed construct. Thus, the clavicle cannot easily rotate while the nail 10 is affixed in place, which aids in healing.

In one embodiment, set forth in FIG. 5, the first bone screw 40 is inserted so as to hold the nail in place in a downward direction, while the second bone screw 42 is inserted so as to hold the nail in a direction that is substantially perpendicular to the first bone screw 40. It will be understood to those of ordinary skill in the art that the size and shape of first bone screw 40 and second bone screw 42 may be modified as desired. For ease of understanding, the first and second bone screws 40, 42 in FIG. 5 are depicted to be larger than may be necessary, depending on the preferences of the user. For example, screws 40, 42 may be about 2 mm in diameter or less, or they may be larger than 2 mm. Desirably, the length of the screws 40, 42 is sufficient to securely hold the nail in place. In some embodiments, it may be desirable for the second bone screw 42 to be inserted from the anterior to the posterior of the subject, or alternatively it may be desirable for the second bone screw 42 to be inserted from the posterior to the anterior of the subject. Other arrangements of screws is of course contemplated, including for example, the use of three screws, each set approximately 60 degree angles from each other. Other similar arrangements of screws or other fixation devices may be incorporated if desired.

The nail 10 of the present invention may be configured with additional features to aid in implantation and follow up after the device has been implanted. For example, the nail and/or the fixation devices may include one or more sensors, radiopaque materials, and the like. These sensors, radiopaque materials and the like may be used to aid during implantation, since the implanter can follow the nail 10 as it is being inserted into the patient. Further, these materials and sensors may be used after implantation to measure migration of the nail as time passes. Further, various sensors may be incorporated into the device so as to determine, for example, the level of force exhibited on the nail at any given time.

The present invention further sets forth various methods of implantation of the nail 10. It will be understood that the methods set forth herein may be manipulated to suit the particular patient and/or implanter. In addition, various steps may be omitted or additional steps may be included, depending on the user's desire. The methods set forth herein describe methods of implantation of the nail 10 into a human clavicle bone, but may be applied to various other similar structures if desired.

The first step in treating the clavicle fracture is to determine the extent and location of the fracture. This is typically done via traditional x-ray. Once the extent and location of the fracture is known, one can determine whether implantation of the inventive intramedullary nail is appropriate.

Once the decision to implant the intramedullary nail has been made, it is desirable to measure the clavicle on the opposite side of the patient (i.e., the non-fracture clavicle). The length of the non-fractured clavicle, the canal distance, and other similar measurements may be taken. By measuring the non-fractured clavicle of the patient, the implanter can implant the nail and structure the bone so that it heals in a similar, if not substantially identical way as the non-fractured clavicle. Measurement of the non-fractured clavicle may be achieved via x-ray, via radiograph, via CT scan, via fluoroscopy, or via any other means desired. Various features may be examined and measured as desired by the user, including cavity diameter, wall thickness, length, and other such features.

Prior to implantation of the nail into the fractured clavicle, the implanter should preferably determine the length, cross section, and degree of curvature of the fractured clavicle. By determining these characteristics of the fractured clavicle, one may select a nail having an appropriate length, cross section, and curvature. As desired by the user, it may be preferable to select a nail having a length slightly longer than the cavity of the bone, so as to allow a portion of the proximal end of the nail to remain outside the cavity. The nail may have pre-drilled holes for affixing the nail once implanted. Alternatively, if no holes are present, the user may wish to drill holes in the nail prior to insertion into the patient.

Once the nail has been selected and prepared, the nail is ready to be implanted. Desirably, the patient is placed in a manner that allows not only placement of the nail and affixation devices, but also allows the implanter to take radiographs during and after placement. Additionally, fluoroscopy may be used to track the implantation of the nail into the clavicle, which requires the patient to be placed in a manner which may allow for viewing. The most desired position has the patient in a position that has the patient sitting in a chair, where the back of the chair is tilted backwards (similar to a beach chair). This position is between the patient laying on his or her back and the patient sitting upright in a chair. Of course, other positions may be used if desired.

Once the patient is in position, the implantation may begin. A small incision is first made into the body of the patient. Desirably the incision is made just off the lateral side of the clavicle (posteriorly), at a location where the clavicle meets the acromion at the acromioclavicular joint (the "AC joint"). Where the acromion meets the clavicle, there is a soft spot in the body. This spot is the desired location for incision and implantation of the nail. The incision is desirably slightly larger than the cross section of the nail, to allow for implantation of the nail while also minimizing the potential for undesirable scarring or nerve damage.

Once the incision is made, a small hole may be drilled through the cortex, in order to install the nail. Once the drilling is complete, the present minimally invasive technique may be employed to reduce the fracture site. For example, the minimally invasive technique may include use of fracture reduction clamps or pointed bone reduction forceps to line up the bone. Once the bone has been aligned properly, the intramedullary nail may be inserted through the incision and through the hole, into the cavity of the clavicle. The nail is inserted from the lateral fragment of the clavicle, across the fracture site, and into the medial fragment. The nail is inserted into the cavity, where it is seated against the end of the medial segment of the clavicle. As explained above, the nail 10 may be inserted any length, and in preferred embodiments the nail 10 is inserted about ⅔ to about ¾ of the length of the cavity. It may be desired, in some instances, to implant the nail so that it is not implanted entirely within the entire length of the cavity, and thus not against the medial segment of the clavicle. The nail is desirably inserted at a controlled, but firm rate, so as to allow the implanter to accurately and completely insert the device. The nail desirably is self-guided, allowing it to manipulate the length of the cavity into which it is being implanted.

During implantation, the implanter may wish to observe and track the implantation of the device to ensure proper insertion. At any point, if the implanter discovers that the device is misaligned or blocked from insertion, the implanter may remove the device or otherwise manipulate the device to allow proper insertion. Use of fluoroscopy is the preferred method of observing implantation; however any known method of tracking surgical implantation is contemplated herein. For example, the observing step may be selected from the group consisting of: observing with x-ray; observing with fluoroscopy; observing through anatomical tests of strength; observing through range of motion; observing the fracture site; and combinations thereof.

The use of the curved nail of the present invention allows for easier and more controlled implantation of the nail into the cavity. Further, the use of materials such as titanium and stainless steel allow the nail to have a slight degree of flexibility, so that the nail can conform to the curve of the clavicle during implantation.

Once the nail is implanted to the desired length, the nail is ready to be affixed in place. Desirably, the nail included holes drilled into it for insertion of affixing means (such as screws). After implantation, the nail may be manipulated by the implanter so as to align the screw holes in the desired location. For example, the implanter may wish to align the holes of the nail so that the screw may be inserted from the front to the back of the patient, or alternatively from the top to the bottom of the patient. Fluoroscopy methods may be useful in aligning the nail so that it may be affixed properly.

It may be desired to reduce or eliminate the gap in the fracture site after implantation. After implanting the nail, but before affixing the nail in place, the distal end of the nail (which is implanted within the medial segment of the clavicle) may be locked and pulled towards the lateral side of the body. Pulling the medial segment of the fractured clavicle compresses the gap between the segments, and thus reduces the risk of distressing the fracture site with the inventive nail. It is preferable to decrease the gap between the segments, as this reduces the risk of nonunion and may aid in allowing the clavicle to return to a strength at or near the strength it had prior to the fracture.

Once the nail has been aligned properly, the implanter may make small incisions at the location of the holes, and use a drill bit to the size of the locking screw (or other attachment means, such as staples) to drill into the clavicle. Once holes have been drilled into and through the clavicle, the affixation means can be inserted through the skin, through the clavicle and through the nail, affixing it in place. In a preferred embodiment, the affixation means include one or more surgical screws having a cross section of about 2 mm. As explained above, it may be most desirable to place one surgical screw approximately perpendicular to a second surgical screw. It is further desirable to place one screw at a location near the proximal end of the nail and a second screw at a location near the distal end of the nail. More screws may be used if desired to fully position the nail in place. Screws may be affixed through any desired means. For example, it may be desired to use radiolucent guide arms or other fluoroscopic guidance to ensure proper fixation of the nail. Any known techniques for affixing intramedullary locking screws may be used in the present invention.

Once the nail has been implanted and affixed, the implanter can again check the implantation via various methods, including radiographs, fluoroscopy or x-ray technology. If the nail is implanted properly, the surgical incisions may be cleaned up and the procedure is complete.

Through the methods and apparatus described herein, healing of the fracture may take about 4 to about 10 weeks to be complete, and desirably takes as few as about 4 to about 6 weeks to be complete. The nail may be permanently attached within the clavicle of the patient, reducing or altogether eliminating the need for additional surgery to remove the nail. Desirably, the patient will maintain his or her arm in a sling for the time period to heal the clavicle, during which movement of the arm is suggested to be limited. Follow up x-rays may be taken at routine intervals after the implantation, to ensure that torsion has not loosened or broken the fixation device.

The present method provides a means to implant a device which not only avoids complications associated with more invasive surgery, but also speeds up the healing process. Through the methods and apparatus used herein, healing may be more desirable, as the present invention provides decreased pain with fixation and an early return to function. That is, movement may be achieved quicker through the use of the present invention and methods than with other methods. In some embodiments, there may be a quicker union of the fractured segments due to the rigid fixation of the fracture. Further, by limiting the amount of incisions or other dissection, the risk of injury to superficial nerves or other potentially harmful techniques. The present methods and techniques promote healing of the body and promote bone regrowth.

It should be understood that various alternatives to the embodiments of the present invention described herein can be employed in practicing the present invention. It is intended that the following list of items help define the scope of the present invention and that structures and methods within the scope of these items and their equivalents be covered entirely.

What is claimed is:

1. An intramedullary nail, comprising:
a pre-curved rod having a proximal end and a distal end, defining a curved nail body therebetween, the curve extending the entire distance between the proximal end and the distal end, said curved nail body having a fixation site along at least one region of the intramedullary nail;
wherein the curved nail body conforms to a curve that has a radius of approximately 60 mm to 180 mm.

2. The intramedullary nail of claim 1, comprising a fixation site at a location near each of said proximal and distal ends.

3. The intramedullary nail of claim 1, wherein the curved nail body conforms to a curve that has a radius of between about 80 mm and about 150 mm.

4. The intramedullary nail of claim 3, wherein the curved nail body has a length of about 70 mm to about 155 mm.

5. The intramedullary nail of claim 1, wherein the curved nail body conforms to a curve that has a radius of between about 80 mm and about 120 mm.

6. The intramedullary nail of claim 5, wherein the curved nail body has a length of about 95 mm to about 130 mm.

7. The intramedullary nail of claim 1, wherein the curved nail body further comprises radiopaque materials located along a portion of said intramedullary nail.

8. The intramedullary nail of claim 1, wherein the curved nail body has a length of about 70 mm to about 155 mm.

9. The intramedullary nail of claim 1, wherein the curved nail body has a length that is between about ⅔ and about ¾ the length of the cavity of the clavicle, said cavity having a length of about of about 85 mm to about 155 mm.

10. The intramedullary nail of claim 1, wherein the intramedullary nail may be adjusted to reduce the size of the intramedullary nail.

11. The intramedullary nail of claim 1, wherein the cross-sectional shape of the nail is cylindrical or elliptical, and the proximal and distal ends are optionally flattened.

12. The intramedullary nail of claim 1, wherein the distal end is tapered and blunted, and the cross-section of the nail is smaller than the diameter of the cavity of the clavicle.

13. A system for intramedullary nail implantation, comprising:
the intramedullary nail of claim 1;
at least one fixation device; and
a means for observing positioning of the intramedullary nail during implantation.

14. A method of implanting a pre-curved, intramedullary nail into a cavity of a fractured clavicle of a subject; comprising the steps of:
providing a intramedullary nail having a first end and a second end, said ends defining a curved nail body therebetween, the curve extending the entire distance between the first end and the second end, wherein the curved nail body conforms to a curve that has a radius of approximately 60 mm to 180 mm
said intramedullary nail having a fixation site towards each of said first and second ends of said intramedullary nail;
implanting said intramedullary nail into the cavity of the fractured clavicle having a fracture site separating the fractured clavicle into a first segment and a second segment, such that said intramedullary nail extends across said fracture site; and
fixing said intramedullary nail at said first segment and said second segment with at least one fixation device at each fixation site of the intramedullary nail.

15. The method of claim 14 wherein said implanting step further comprises implanting the intramedullary nail percutaneously.

16. The method of claim 14, wherein the implanting step further comprises implanting the intramedullary nail through the lateral end of the clavicle.

17. The method of claim 14, further comprising the step of observing the intramedullary nail during implantation.

18. The method of claim 14, wherein the curved nail body conforms to a curve that has a radius of between about 80 mm and about 120 mm.

19. The method of claim 14, further comprising the step of determining the curvature, length and diameter of a clavicle of the subject, or of the cavity of a clavicle of the subject.

20. The method of claim 19, further comprising the step of selecting an intramedullary nail having a curvature conforming to the curvature of the clavicle or of the cavity of the clavicle, a length of between about ⅔ and about ¾ the length of the cavity of the clavicle and a cross section about 1 to about 4 mm smaller than the diameter of the cavity of the clavicle.

21. The method of claim 19, further comprising the step of selecting an intramedullary nail having a curvature conforming to the curvature of the clavicle or of the cavity of the clavicle, a length of between about 70 mm to about 155 mm, and a cross section about 1 to about 4 mm smaller than the diameter of the cavity of the clavicle.

\* \* \* \* \*

UNITED STATES PATENT AND TRADEMARK OFFICE
CERTIFICATE OF CORRECTION

| | | |
|---|---|---|
| PATENT NO. | : 9,510,878 B2 | Page 1 of 1 |
| APPLICATION NO. | : 13/510241 | |
| DATED | : December 6, 2016 | |
| INVENTOR(S) | : Nanavati et al. | |

It is certified that error appears in the above-identified patent and that said Letters Patent is hereby corrected as shown below:

In the Specification

Column 2, Line 10:
Now reads: "...dissection and about the..."
Should read: -- ...dissection about the... --

Column 5, Line 65:
Now reads: "...may drilled immediately..."
Should read: -- ...may be drilled immediately... --

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*